United States Patent [19]

Youngman et al.

[11] 4,311,517

[45] Jan. 19, 1982

[54] REDUCING THE EFFECT, IN PLANTS, OF ICE-PROMOTING NUCLEI ORIGINATING FROM CERTAIN BACTERIA

[75] Inventors: Edward A. Youngman, Modesto, Calif.; Russell C. Schnell, Boulder, Colo.

[73] Assignee: Shell Oil Company, Houston, Tex.

[21] Appl. No.: 126,635

[22] Filed: Mar. 3, 1980

[51] Int. Cl.³ .......................................... A01N 33/12
[52] U.S. Cl. ..................................... 71/121; 424/329
[58] Field of Search ......................... 424/329; 71/121

[56] References Cited

PUBLICATIONS

McCutcheon's Functional Materials (1979).

*Primary Examiner*—Catherine L. Mills

[57] ABSTRACT

Ice-promoting nuclei resulting from the presence of certain bacteria on cold-sensitive plants are eliminated by treating the plants with one or more of certain cationic quaternary ammonium surfactants.

3 Claims, No Drawings

REDUCING THE EFFECT, IN PLANTS, OF ICE-PROMOTING NUCLEI ORIGINATING FROM CERTAIN BACTERIA

BACKGROUND OF THE INVENTION

When a temperate-climate, cold-sensitive plant is subjected to a low temperature, the plant is injured only if freezing of the intercellular liquid in the plant tissues occurs. As the plant is cooled, the intercellular liquid will supercool, unless ice crystals form on the external surface of the plant at a location where the crystals can readily penetrate into the intercellular liquid—as in the stomatal cavities, on the under surfaces of leaves and/or in the basal portions of flowers. Such ice crystals propagate into the intercellular liquid, initiating freezing therein. Such external water also supercools to temperatures as low as about −8° C., unless there are present nuclei which act to initiate crystallization at a higher temperature.

Two species of bacteria, out of many species of bacteria, that commonly are present of the above-ground portions of plants—i.e., the bacteria *Erwinia herbicola* and *Pseudomonas syringae*—provide nuclei which initiate the formation of ice crystals, and cause injury to sensitive plants at relatively high temperatures—i.e., −2° C. to −5° C.: Lindow, S. E. et al., "The Role of Bacterial Ice Nuclei in Frost Injury to Sensitive Plants", being pages 249-263 of "Plant Cold Hardiness and Freezing Stress", Li, P. and Sakai, A., editors, Academic Press, 1978.

To protect plants from frost damage, it is therefore desirable to have available means for reducing the ice-promoting effects of these bacteria.

DESCRIPTION OF THE INVENTION

It now has been found that the effectiveness of both *E. herbicola* and *P. syringae* in initiating freezing in the tissues of a plant is significantly reduced, and the possibility of frost damage to the plant is accordingly reduced, by treating the above-ground portion of the plant, before it is subjected to a temperature below about 0° C., with an effective amount of one or a mixture of two or more cationic quaternary ammonium surfactants of the formula:

wherein $R^1$ is alkyl, alkenyl or alkylphenalkyl of 8 to 20 carbon atoms, phenalkyl of 7 to 20 carbon atoms, $R^2$ and $R^3$ each is alkyl of 1 to 6 carbon atoms, $R^4$ is alkyl, alkenyl, phenalkyl or alkylphenalkyl of 1 to 20 carbon atoms, and X is an anion.

Accordingly, the invention provides a method for significantly reducing the ice-promoting effect of the bacteria *Erwina herbiocola* and *Pseudomonas syringae* on plants, which comprises applying to the above-ground portion of the plant infested with one or both of such species of bacteria, an effective non-phytotoxic amount of one or more of the quaternary ammonium compounds of Formula I.

Stated in a different way, the invention provides a method for minimizing damage in a plant to be subjected to a low temperature, which plant is infested with one or both of the species of bacteria *Erwinia herbicola* and *Pseudomonas syringae*, which comprises applying to the above-ground portion of the plant, before it is subjected to the low temperature, one or more of the quaternary ammonium compounds of Formula I, the amount of said compound being sufficient to significantly reduce the ice-nucleating effect of said bacteria but not being significantly toxic to the plant.

Such quaternary ammonium compounds are commonly known as "quats", and for the sake of brevity the contemplated compounds of this class hereinafter will be denoted as such.

In these quats, the alkyl and alkenyl moieties suitably are either straight-chain or branched-chain in configuration. Preferably, $R^2$ and $R^3$ each is methyl. Also, for ease in application of the quat, it is desirable that the quat be substantially soluble in water. Therefore, it is preferred that the total number of carbon atoms in the moieties $R^1$ and $R^4$ not exceed about thirty. This is not to say, however, that quats wherein these moieties together contain more than thirty carbon atoms (as in dimethyldioctadecylammonium chloride) are not effective for attaining the purposes of the invention, but merely that for application such quats would have to be formulated as suspensions, rather than as solutions, in water.

Generally, although not necessarily, these quats are derived from naturally-occurring fatty acids, such as derived from coconut oil, tallow, hydrogenated tallow, palm oil, and the like, so that the quat product may be a mixture of the compounds of Formula I in which the alkyl and/or alkenyl moieties correspond to those in the fatty acid precursors. The product suitably also can contain minor amounts of the corresponding quats wherein the alkyl and/or alkenyl moiety is of lower- or higher-molecular weight than those specified in Formula I, these quats resulting when the product is derived from a naturally-occurring material. In quats derived from such materials, the alkyl and/or alkenyl moeities will be a moiety such as capric, lauric, myristic, palmitic, stearic, dodecyl, decylenic, dodecylenic, palmitoleic, oleic, ricinoleic, linolenic, petroselenic, linoleic, eleostearic and the like.

Mixtures of two or more different quats of Formula I are suitable.

The anion suitably is that of any organic or inorganic acid, that is not phytotoxic, the character of the anion apparently not affecting the bactericidal activity of the compound, but affecting its solubility in water. The commercial products are mostly the bromides or chlorides, and because of their availability and relatively low cost, are to be preferred.

Of particular interest because of their effectiveness for the purposes of the invention, and because of their ready availability are the quats of the formula

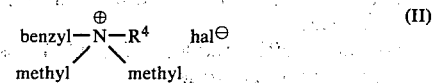

wherein $R^4$ is alkyl or alkenyl of from eight to eighteen carbon atoms, and "hal" is chlorine or bromine.

Quats of Formulae I and II are well known in the art, being sold commercially as antimicrobials, specifically as fungicides, bactericides, disinfectants and/or algaecides, being listed in such publications as McCutcheon's Functional Materials, as "Antimicrobials" and "Fungicides" (1979), and McCutcheon's Detergents and Emulsifiers, International, under "Chemical Classification", "Quaternary Surfactants" (1979).

Examples of such quats are the following, identified by tradename and identity:

Benzalkonium chloride (generic name for alkyl dimethyl benzyl ammonium chlorides)
Alkyl dimethyl benzyl chlorides, such as:
  Alkaquat DMB 451;
  Arquad B-100;
  Barquat MB-50, MX-50, OJ-50;
  Bio-Quat 50-24, 80-24,
  BTC 50, 824, 8248;
  Maquat 11-12S, MC-1412;
  Germ-I-Tol and Neo-Germ-I-Tol;
  Alkaquat DMB 451;
  Catigene T/80+T/50;
  Cation G-40;
  Cycloton B50;
  Gardiquat 1450, A 50;
  Latensit K-LC, K-OC;
  Nissan Cation F$_2$-50, M$_2$-100;
  Quadrilan BC.
Aliquat H 226—dimethyl di(hydrogenated tallow) ammonium chloride.
  Aliquat 26—trimethyl tallow ammonium chloride.
  Aliquat 221—dimethyl dicoco ammonium chloride.
  Bardac LF—dioctyl dimethyl ammonium chloride.
  Bardac 20—octyl decyl dimethyl ammonium chloride.
  Bardac 22—didecyl dimethyl ammonium chloride.
  Barquat MS-100—myristyl dimethyl benzyl ammonium chloride.
  Barquat 4250, 4280, 4250Z, 4280Z—mixtures of the alkyl dimethyl benzyl ammonium chloride and dimethyl ethyl benzyl ammonium chloride.
Bio-Quat 50-35—mixture of alkyl dimethyl benzyl ammonium chloride and dimethyl ethylbenzyl ammonium chloride.
Bio-Quat 50-MAB—alkyl dimethyl ethyl ammonium bromide.
Bio-Quat T-501—mixture of alkyl dimethyl benzyl ammonium chloride and alkyl dimethyl benzyl ammonium bromide.
Bretol—cetyl dimethyl ethyl ammonium bromide.
Bromat—cetyl trimethyl ammonium bromide.
BTC 471—alkyl dimethyl ethylbenzyl ammonium chloride.
BTC 824—tetradecyl dimethyl benzyl ammonium chloride mono hydrate.
BTC 1010—didecyl dimethyl ammonium chloride.
BTC 2125 and 2125M—mixtures of alkyl dimethyl benzyl ammonium chloride and alkyl dimethyl ethylbenzyl ammonium chloride.
Cetol—cetyl dimethyl benzyl ammonium chloride.
Dibactol—myristyl dimethyl benzyl ammonium chloride.
Hyamine 3500—alkyl($C_{12}$, $C_{14}$, $C_{16}$) dimethyl benzyl ammonium chloride.
Maquat SC-18—stearyl dimethyl benzyl ammonium chloride.
Maquat MQ-2525—mixture of n-alkyl dimethyl benzyl ammonium chloride and n-alkyl dimethyl ethylbenzyl ammonium chloride.
Maquat TC-76—6:1 mixture of n-alkyl dimethyl benzyl ammonium chloride and di-(n-alkyl) methyl benzyl ammonium chloride.
Mytab—myristyl trimethyl ammonium bromide
Roccal II—Benzalkonium chloride.
Stedbac—stearyl dimethyl benzyl ammonium chloride.
Vanquat 50 MC—($C_{12}$ to $C_{16}$) alkyl dimethyl benzyl ammonium chloride.
Adogen 442—dimethyl di(hydrogenated tallow) ammonium chloride.
Adogen 444—trimethyl palmitic ammonium chloride.
Adogen 471—trimethyl tallow ammonium chloride.
Arquad B-50—($C_8$-$C_{18}$)alkyl dimethyl benzyl ammonium chloride.
Arquad DMMCB-50—($C_{12}$-$C_{14}$-$C_{16}$)alkyl dimethyl benzyl ammonium chloride.
Arquad DM14B—Myristyl dimethyl benzyl ammonium chloride dihydrate.
Arquad DMHTB—hydrogenated tallow dimethyl benzyl ammonium chloride.
Catigene BR/80B—alkyl dimethyl benzyl ammonium bromide.
Catigene 4513+453/80—mixture of alkyl dimethyl benzyl ammonium chloride and alkyl dimethyl ethylbenzyl ammonium chloride.
Catinal CB-50—lauryl dimethyl benzyl ammonium chloride.
Catinal HTB and HTB-70—alkyl trimethyl ammonium bromide.
Catinal DB-80E—stearyl dimethyl benzyl ammonium chloride.
Cation S—stearyl dimethyl benzyl ammonium chloride.
Cation DS—distearyl dimethyl ammonium chloride.
Cycloton V—alkyl trimethyl benzyl ammonium bromide.
Dehyquart A—cetyl trimethyl ammonium chloride.
Dehyquart CDB—cetyl dimethyl benzyl ammonium chloride.
Dehyquart DAM—dialkyl dimethyl ammonium chloride.
Dehyquart LDB—lauryl dimethyl benzyl ammonium chloride.
Dehyquart LT—lauryl trimethyl ammonium chloride.
Empigen BAL—benzalkonium chloride.
Genamin DSAC—dialkyl dimethyl ammonium chloride.
Kemamine:
  BAC—benzalkonium chloride;
  BQ 6902C—benzyl dimethyl dodecyl ammonium chloride;
  BQ 8802C—benzyl dimethyl hexadecyl ammonium chloride;
  BQ 6502C—benzyl dimethyl coconut ammonium chloride;
  BQ 9742C—benzyl dimethyl tallow ammonium chloride;
  BQ 9702C—benzyl dimethyl hydrogenated tallow ammonium chloride;
  Q 6903B, Q 7903B, Q 8803B, Q 9903B, Q 6503B, Q 9743B, Q 9703B, Q 9973B—trimethyl R ammonium chlorides wherein R is dodecyl, tetradecyl, hexadecyl, octadecyl, coconut, tallow, hydrogenated tallow and soya, respectively;
  Q 6502B,—dimethyl dicoconut ammonium chloride;
  QSML2—dimethyl di(hydrogenated tallow) ammonium chloride.
Lebon GM—benzalkonium chloride.

Loraquat B18—alkylbenzyl trimethyl ammonium chloride.

Nissan Cation AB, BB, PB-40—trimethyl octadecyl, dodecyl, and hexadecyl ammonium chlorides, respectively.

Noramium:
  C 85, S 75, D 85—dimethyl benzyl coco, tallow, and oleyl ammonium chlorides, respectively;
  M 2C and M 2SH—dimethyl dicoco and (di(hydrogenated tallow) ammonium chlorides, respectively;
  MC 50, MSH 50 and MD 50—trimethyl coco, hydrogenated tallow, and oleyl ammonium chlorides, respectively.

Quartamin:
  DCP, D86P—dimethyl di-coco, and di-stearyl ammonium chlorides, respectively;
  CPR, TPR, HTPR—alkyl trimethyl ammonium chlorides wherein the alkyl is coconut, tallow and hydrogenated tallow, respectively.

Sanisol
  CR, CPR, TPR, OPR—alkyl dimethyl benzyl ammonium chlorides wherein the alkyl is coconut, tallow, oleyl and hydrogenated tallow, respectively.

Servamine KAC 412—coco trimethyl ammonium chloride.

Servamine KAC 422—coco dimethyl benzyl ammonium chloride.

Sokalan WM—dimethyl distearyl ammonium chloride.

Steinquat BSD—lauryl dimethyl benzyl ammonium chloride.

Steinquat QA 100—alkyl dimethyl benzyl saccharinate.

Swanol CA-101—dodecyl dimethyl benzyl ammonium chloride.

Tequat BC—cetyl trimethyl ammonium chloride.

Tequat PAN—lauryl dimethyl benzyl ammonium chloride.

Vantoc AL, N—alkyl trimethyl ammonium bromide.

Vantoc CL—lauryl dimethyl benzyl ammonium chloride.

Ammonyx T, KP, 4002—dimethyl benzyl cetyl, oleyl, stearyl ammonium chlorides, respectively.

Alocsan DBC-50—dodecylbenzyl trimethyl ammonium chloride.

Barquat BT-60—benzyl trimethyl ammonium chloride.

Such quats have been found to significantly diminish the effectiveness of *E. herbicola* and *P. syringae* for initiating ice formation. The mechanism by which they accomplish this has not been determined. Typical individual species of these quats were examined on the basis of the following criteria:

(a) their effectiveness in killing or halting growth of *Erwinia herbicola* (hereinafter *E.h.*) and *Pseudomonas syringae* (herein-after *P.s.*);

(b) their effectiveness in eliminating—i.e., passivating or deactivating—the ice-nucleating effect of the two species of bacteria;

(c) the time that they require to accomplish (a) and (b). This factor has a bearing on whether the quats can be used effectively only when applied a relatively short time before the plant is to be subjected to cold stress, or whether it can be used ahead of time to provide prophylactic protection for the plants.

The tests were conducted as follows:

GROWTH TESTS

Test Procedure A

Designed to determine the efficacy of a chemical as a prophylactic in killing or inhibiting the growth of the bacteria, and/or eliminating the effect of the bacteria-derived ice nuclei. Such chemicals could have application in situations where it is desirable to provide protection for a plant by applying the chemical some time before the plant is to be subjected to a below-zero temperature.

A stock solution containing one percent by weight of a test chemical in an inert solvent (water or 1:1 (v/v) DMSO:acetone) was prepared, filtered and sterilized. Enough of the stock solution was mixed with a standard amount of sterilized Koser Citrate Broth (KCB) to provide the desired (standard) concentration of the test chemical in the resulting solution.

Each of the resulting cultures was inoculated with approximately $10^6$ bacteria of the species *E.h.* (in one series of tests) and *P.s.* (in another series of tests). (The number of bacteria was selected to approximate bacteria concentrations which one might expect is on actively growing leaf culture early in the growing season.) The inoculated cultures were incubated (rotary shaker, room temperature). The results were read after 1, 4 and 7 days incubation, respectively. Visible turbidity in the culture was the criterion: cultures which were not turbid after 7 days were recorded as having no growth of the bacteria. In control cultures containing no test chemical, the bacteria grew profusely in one day.

The tests were replicated to ensure repeatability.

Test Procedure B

Designed to determine the efficacy of a chemical for eliminating the ice-nucleating effect of the bacteria immediately after application of the chemical. Such a chemical would be desirable to protect a plant from frost on short notice.

A sample of a culture of either *E.h.* or *P.s.* known to have a certain minimum ice-nucleating activity was added to a standard amount of KCB containing a standard concentration of test chemical. The resulting inoculated culture was incubated (*E.h.* at room temperature; *P.s* at 4° C.) and examined in a nucleus spectrometer at 1, 2, 6 and 24 hours for *E.h.* and at 1, 6 and 24 hours for *P.s.* For each sample, 10 drops of 0.1 ml each were tested. The spectrometer was cooled at one degree Centigrade per minute. Two temperatures were recorded: $T_1$ and $T_{90}$. (Separate drops of distilled water containing a common ice nucleant freeze over a range of temperatures. The temperature at which the first drop freezes is designated as $T_1$ and the temperature at which 90% of the drops in the sample freeze is designated as $T_{90}$. Statistically, and from experience, the $T_{90}$ of a sample has been found to be the best measure of a sample's ice nucleating effectiveness).

The cultures in these tests contained about $10^8$ bacteria per milliliter, to duplicate the maximum number of bacteria that might occur in nature on plants to be protected from frost.

The tests were replicated to ensure repeatability.

Controls

Two sets of controls were run.

(a) culture plus KCB, no test compound. $T_{90}$'s were determined, and used in ascertaining the effectiveness of each test chemical.

(b) test compound plus KCB, no bacteria. To determine if the test chemical had any ice-nucleating effect. None did.

The following compounds of Formula I were tested:

| Material | Identity |
|---|---|
| A | Magna M 407 - commercial product, active material characterized as an alkyldimethylbenzyl ammonium chloride (chain-length of the alkyl moiety not specified.) |
| B | Petrolite/Tretolite WF-88 - developmental product active material characterized as a ($C_{12}$, $C_{14}$, $C_{16}$-alkyl)dimethylbenzylammonium chloride. |
| C | Petrolite/Tretolite WF-828 - similar to WF-88. |
| D | Petrolite/Tretolite XC-503 - now-discontinued commercial product, active material characterized as an oleyl dimethylbenzylammonium chloride, active content: 15% w. |
| E | Petrolite/Tretolite XC-511 - commercial product, active material characterized as alkyl ($C_{12}$-60%, $C_{14}$-23%, $C_{16}$-11%, $C_8 + C_{10}$-2.5%, $C_{18}$-2.5%)dimethylbenzyl ammonium chloride. |
| F | (9-octadecenyl)dimethylbenzylammonium chloride. |
| G | Arquad C50 - commercial product, active material characterized as cocotrimethylammonium chloride. |
| H | Petrolite/Tretolite XC-507 - commercial product, active material characterized as didecyldimethylammonium chloride. |

The results of testing these materials according to Test Procedure A are summarized in Table I.

TABLE I

| | Test Organism | | | |
|---|---|---|---|---|
| | E. herbicola Concentration of test material (%) | | P. syringae Concentration of test material (%) | |
| Material | 0.001 | 0.01 | 0.001 | 0.01 |
| A | 1[a] | NG[b] | 1 | NG |
| B | NG | NG | NG | NG |
| C | 4 | NG | NG | NG |
| D | NG | NG | NG | NG |
| E | 4 | NG | — | 5[c] |
| G | — | 4[c] | 4 | NG |
| H | NG | NG | NG | NG |
| Control (no chemical) | 1 | 1 | 1 | 1 |

[a]Number indicates number of days of incubation required for turbidity. Turbidity was read at 1, 4 and 7 days, except in the case of material E, where the turbidity was read each day.
[b]NG signifies no growth.
[c]No growth at 0.02%.

The results of testing these materials according to Test Procedure B are summarized in Table II.

TABLE II

| | $T_{90}$ (−°C.) After Incubation For The Indicated Period | | | | | | |
|---|---|---|---|---|---|---|---|
| | P. herbicola | | | | P. syringae | | |
| Material | 1 hr. | 6 hr. | 24 hr. | 48 hr. | 1 hr. | 6 hr. | 24 hr. |
| A | 7.1 | 7.8 | 8.3 | 7.4 | 7.0 | 7.0 | 8.0 |
| B | 7.5 | 8.2 | 8.4 | 7.4 | 7.1 | 8.8 | 7.8 |
| C | 7.6 | 7.6 | 8.2 | 7.4 | 7.0 | 8.4 | 7.7 |
| D | 8.4 | 8.9 | 8.3 | 10.1 | 9.3 | 8.2 | 13.6 |
| G | 7.2 | 7.9 | 7.0 | 7.3 | 7.0 | 7.4 | 7.3 |
| H | 7.7 | 7.7 | 7.5 | 8.0 | 8.4 | 7.9 | 8.0 |
| None (Control) | 4.5 | 4.1 | 3.6 | 4.1 | 5.1 | 5.4 | 2.9 |
| E[a] | | 7.9 | 8.0 | | | 5.7 | 5.5 |
| None | | 3.3 | 3.3 | | | 3.2 | 2.8 |
| (Control) | | | | | | | |

[a]Materials A, B, C, D, G and H were tested in one test series; material E was tested in a second test series.

Materials A, B, C and D were tested by the same procedure in another test series, the results being reported in Table III.

TABLE III

| | $T_{90}$ (−°C.) After Incubation For The Indicated Period | | | |
|---|---|---|---|---|
| | P. herbicola | | P. syringae | |
| Material | 6 hr. | 24 hr. | 6 hr. | 24 hr. |
| A | 16.4 | 10.1 | 7.7 | 7.8 |
| B | 21.4 | 20.7 | 7.4 | 7.5 |
| C | 18.5 | 17.6 | 7.9 | 7.6 |
| D | 23.5 | 21.3 | 9.8 | 10.7 |
| None (Control) | 8.1 | 8.4 | 3.3 | 3.0 |

Materials D and F were tested in another procedure:

The test organisms were E. herbicola and P. syringae 31. Inocula were grown overnight at 22° C. with aeration. P.s. was grown in KCB; E.h. was grown in Trypticase Soy Yeast Extract Broth (TSY; 0.05% BBL Trypticase Soy Broth, 0.2% BBL Yeast Extract). Cultures were grown to a standard turbidity (optical density of 0.83–0.85 at 450 nm). 0.5 milliliter of the inoculum was added to 4.5 milliliters of the appropriate broth containing the test material. The test materials were in solution in water. The culture then was incubated for 24 hours at 22° C. in a shaker, and tested in the nucleus spectrometer to ascertain the $T_{90}$ temperature.

Also, after the incubation, the culture was tested for viability of the bacteria, by placing drops of the culture on TSY agar, incubating the inoculated agar overnight at 22° C. and evaluating the results as growth or no growth.

The results are reported in Table IV.

TABLE IV

| Material | Dosage (ppm) | P.s. $T_{90}$(−°C.) | Growth[a] | E.h. $T_{90}$(−°C.) | Growth |
|---|---|---|---|---|---|
| D | 100 | 9.97 | — | 9.10 | — |
| | 200 | 12.51 | — | 10.44 | — |
| | 400 | 13.21 | — | 15.01 | — |
| | 600 | 9.85 | — | 14.76 | — |
| | 800 | 13.58 | — | 20.32 | — |
| | 1000 | 14.58 | — | 20.04 | — |
| F | 15 | 3.36 | + | 5.21 | + |
| | 30 | 7.63 | + | 4.88 | + |
| | 45 | 7.90 | + | NT[b] | NT |
| | 60 | 8.93 | — | 7.40 | + |
| | 90 | 10.34 | + | 8.41 | + |
| | 120 | 8.21 | — | 8.27 | + |
| | 150 | 7.86 | — | 8.92 | + |
| | 300 | 10.16 | — | 14.00 | — |
| None (Control) | | 3.31 | + | 3.54 | + |

[a] + = growth; − = no growth.
[b]NT = not tested.

To ascertain if significant numbers of either or both of E. herbicola and P. syringae are present on a plant, so that treatment of the plant according to the method of the invention is needed, the test procedures for the controls set out hereinbefore can be used.

To reduce the effect of the bacteria upon the plant, and thus protect the plant from low temperatures, the quat is applied to the above-ground surfaces of the plant. Any conventional technique may be used that will result in as complete coverage as possible of the plant surfaces by the quat. In many cases, the necessary coverage may be attained by spraying the above-ground portions of the plant to run-off with a solution of the quat in water. Since these quats may be phytotoxic, it is desirable to employ the minimum dosage thereof that will provide the required safening effect. Generally, this requires a concentration of at least about 0.001 percent by weight of the quat in the solution. Also, in general, it will be found that the concentration of the quat need not exceed about five percent, on the same basis. Generally, a solution containing from about 0.01 to about 1% by weight of the quat will be found to be suitable.

The quat may be applied by other conventional methods, as by electrostatic techniques, by ultra-low volume (ulv) techniques or the like.

The quats themselves are surfactants, and are water-soluble, so that a simple solution of the quat in water will generally be found to be most desirable, from the standpoint of cost. If needed, a sticker may be added, or a co-solvent added. The quat can be formulated as a dust, if desirable, or where it is of limited solubility in water, as a suspension. If any such adjuvant or carrier—solid or liquid—is added, its effect upon the effectiveness of the quat, should be ascertained before the formulation is used. In this regard, the quats, being cationic in character, in general will be incompatible with soaps, and other anionic materials. Also, it is possible that the adjuvant or carrier may have an effect upon the phytotoxicity of the quat—a factor that also should be taken into account.

The quats reduce the effect of the bacteria quite rapidly. Thus, they may be applied shortly before—for example, within four hours before—onset of the low temperature is expected. On the other hand, they retain their effectiveness for some time, so that they may be applied several days before the expected onset of low temperature.

Since the involved bacteria can re-establish themselves in significant numbers fairly rapidly, it may be desirable to check the plants for the presence of significant numbers of the bacteria shortly before the expected onset of the low temperature, to determine if retreatment is needed.

We claim:

1. A method for minimizing damage in a plant to be subjected to a low temperature, which plant is infested with one or both of the species of bacteria *Erwinia herbicola* and *Pseudomonas syringae*, which comprises applying to the above-ground portion of the plant before it is subjected to the low temperature a compound of the formula $$R^1 - \overset{\oplus}{\underset{\underset{R^2}{\diagup} \phantom{N} \overset{\diagdown}{R^3}}{N}} - R^4 \quad X^{\ominus} \qquad (I)$$

wherein $R^1$ is alkyl, alkenyl or alkylphenalkyl of 8 to 20 carbon atoms, or phenalkyl of 7 to 20 carbon atoms, $R^2$ and $R^3$ each is alkyl of 1 to 6 carbon atoms, $R^4$ is alkyl, alkenyl, phenalkyl or alkylphenalkyl of 1 to 20 carbon atoms, and X is an anion, the amount of said compound being sufficient to significantly reduce the ice-nucleating effect of said bacteria but not being toxic to the plant.

2. A method according to claim 1 wherein $R^1$ is benzyl, $R^2$ and $R^3$ each is methyl, $R^4$ is alkyl or alkenyl of from 8 to 18 carbon atoms, and X is halide ion.

3. A method according to claim 2 wherein the moiety $R^4$ contains from 12 to 18 carbon atoms.

* * * * *